(12) United States Patent
Andersson et al.

(10) Patent No.: US 8,574,569 B2
(45) Date of Patent: *Nov. 5, 2013

(54) STABILIZED PROTEASE COMPOSITION

(71) Applicant: Trobio AB, Nacka (SE)

(72) Inventors: Lars-Olov Andersson, Nacka (SE); Hans Ageland, Saltsjo-Boo (SE)

(73) Assignee: Trobio AB, Nacka (SE)

( * ) Notice: Subject to any disclaimer, the term of this patent is extended or adjusted under 35 U.S.C. 154(b) by 0 days.

This patent is subject to a terminal disclaimer.

(21) Appl. No.: 13/760,148

(22) Filed: Feb. 6, 2013

(65) Prior Publication Data

US 2013/0157339 A1    Jun. 20, 2013

Related U.S. Application Data

(63) Continuation of application No. 11/992,061, filed as application No. PCT/SE2005/001391 on Sep. 22, 2005, now Pat. No. 8,394,372.

(51) Int. Cl.
 *A61K 38/54* (2006.01)
 *C12N 9/96* (2006.01)

(52) U.S. Cl.
 USPC .......................... 424/94.3; 435/188; 435/214

(58) Field of Classification Search
 USPC ................... 424/94.3; 435/188, 214
 See application file for complete search history.

(56) References Cited

U.S. PATENT DOCUMENTS

| | | | |
|---|---|---|---|
| 5,409,927 | A | 4/1995 | Bold et al. |
| 5,773,608 | A | 6/1998 | Yen et al. |
| 5,879,923 | A | 3/1999 | Yago et al. |
| 6,177,126 | B1 | 1/2001 | Hagedorn et al. |
| 6,177,268 | B1 | 1/2001 | Yonehara |
| 6,376,648 | B2 | 4/2002 | White et al. |
| 6,992,172 | B1 | 1/2006 | Chang et al. |
| 7,351,561 | B2 | 4/2008 | Metzner et al. |
| 2001/0033837 | A1 | 10/2001 | Metzner et al. |
| 2003/0031718 | A1 | 2/2003 | Wong et al. |
| 2003/0147878 | A1 | 8/2003 | Wadstrom |
| 2004/0118778 | A1 | 6/2004 | Qian et al. |
| 2006/0034930 | A1 | 2/2006 | Khosravi et al. |
| 2006/0270014 | A1 | 11/2006 | Pawlak et al. |

FOREIGN PATENT DOCUMENTS

| | | | |
|---|---|---|---|
| CN | 1504580 | A | 6/2004 |
| EP | 1136084 | A1 | 9/2001 |
| EP | 1418182 | A1 | 5/2004 |
| EP | 1637141 | A1 | 3/2006 |
| JP | 11-147834 | A | 6/1999 |
| JP | 2002-3353 | A | 1/2002 |
| JP | 2002-516566 | A | 6/2002 |
| JP | 2002-526531 | A | 8/2002 |
| JP | 2004-509104 | A | 3/2004 |
| JP | 2004-517060 | A | 6/2004 |
| JP | 2004-191367 | A | 7/2004 |
| WO | WO 98/22619 | A1 | 5/1998 |
| WO | WO 99/11658 | A1 | 3/1999 |
| WO | WO 00/20394 | A1 | 4/2000 |
| WO | WO 02/22575 | A | 3/2002 |
| WO | WO 02/37937 | A2 | 5/2002 |
| WO | WO 02/100830 | A | 12/2002 |
| WO | WO 03/016347 | A1 | 2/2003 |

OTHER PUBLICATIONS

Alrdich Catalog (1996-1997) p. 88.
Chinese Office Action for Appl. No. 200580051655.0 dated Apr. 22, 2010.
Derwent abstract for SU 833985 B Bondarev et al., May 30, 1981 (downloaded from Derwent Feb. 25, 2001).
Dewent abstract for JP 2004191637 downloaded from WEST Mar. 20, 2012.
English language Japanese Office Action, dated Aug. 23, 2011, for Japanese Application No. 2008-532186.
English machine translation for JP 2004191637 downloaded from the JPO Mar. 20, 2012.
EPO International Preliminary Report on Patentability for Appl. No. PCT/SE2005/001391 dated Aug. 23, 2007.
EPO International Search Report for Appl. No. PCT/SE2005/001391 dated Feb. 15, 2006.
Kikugawa, N., "Thrombin reagent and test reagent kit," CA, 2004, XP002337251.
Lehninger "Biochemistry" (1975) 2nd edition. (Worth Publishers, Inc.: New York, NY) p. 51-52, 197.
Markwardt et al., European J. Biochem (1968) 6: 502-506.
Nakamura et al., "Characterization of p-aminobenzamidine-based sorbent and its use for high-performance affinity chromatography of trypsin-like proteases", Journal of Chromatography A, 1009, 2003, pp. 133-139.
Sigma Catalog (1998) p. 1876.
Turner et al., "p-Amidino Esters as Irreversible Inhibitors of IXa and Xa and Thrombin", Biochemistry, 1986, 25, pp. 4929-4935, XP000608122.
von der Saal et al., Bioorganic Med. Chem. Lett. (1997) 7(10): 1283-1288.
Yang et al., "Synthesis of Novel Biodegradable Cationic Polymer: N,N-Diethylethylenediamine Polyurethane as a Gene Carrier", Biomacromolecules 2004, vol. 5, pp. 1926-1932.

*Primary Examiner* — Susan Hanley
(74) *Attorney, Agent, or Firm* — Birch, Stewart, Kolasch & Birch, LLP

(57) ABSTRACT

A composition is provided, which comprises a serine protease; a reversible inhibitor of said serine protease; and a stabilizing agent M having the formula I:

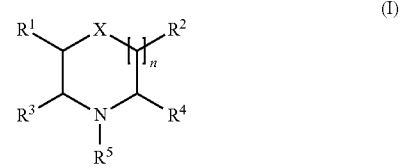

(I)

Also provided are uses of the composition as a medicament, and other uses and methods employing its various properties.

18 Claims, No Drawings

STABILIZED PROTEASE COMPOSITION

This application is a Continuation of U.S. application Ser. No. 11/992,061 filed Mar. 14, 2008, which issued as U.S. Pat. No. 8,394,372 on Mar. 12, 2013, which is the National Phase of PCT/SE2005/001391, filed Sep. 22, 2005. All of the above applications are hereby expressly incorporated by reference into the present application.

FIELD OF THE INVENTION

The present invention relates to an enzyme composition in which the enzyme is stabilized by certain additives in an inventive combination. More particularly, the invention concerns a serine protease composition comprising a reversible inhibitor to the serine protease and an additional stabilizing agent M as defined below.

BACKGROUND

Serine proteases are a group of proteolytic enzymes characterized by having a serine and a histidine residue in their active site. Many well known enzymes belong to this group, for example trypsin, kallikrein, thrombin and plasmin. Several of them have found practical use. Trypsin is used in the leather industry. Thrombin is used as a haemostatic agent to stop bleeding from wounds. Urokinase and tissue plasminogen activator, two other serine proteases, are used clinically as thrombolytic agents in the treatment of acute myocardial infarction. A number of these enzymes have been used extensively as research tools, for instance in protein structure determination. Furthermore, the enzymes are used in various diagnostic kits.

Common to most of the serine proteases are their limited stability in solution. This is mainly caused by autodegradation when left in solution, caused by their property as proteases. This limited stability is a problem when the material has to be stored in solution. Commercial serine protease preparations available today are essentially always in the form of frozen solutions or lyophilized powders, with obvious drawbacks. The extra time needed for dissolution of the powder or thawing of the frozen solution to the correct temperature is the most important issue. There are, however, other problems with these preparations. For frozen solutions, there is a need for controlled temperatures (−20° C.) in all steps from manufacture and transportation to storage. For lyophilized powders, there is a need for a reconstitution solution with an acceptable grade of purity and stability. Also, the material frequently needs to be prepared aseptically (by mixing of the two parts) in an environment which may be non-controlled (such as inclement weather or lack of a clean water supply), and there is a need to verify that the powders have been properly mixed. These are all major drawbacks of the products available today, adding to their complexity of use as well as their cost.

For thrombin, which preferably has to be immediately available for use in arresting bleeding, the stability problems have forced manufacturers to use lyophilized thrombin or deep frozen solutions. These then require a certain amount of time to prepare for use. The two thrombolytic agents urokinase and tissue plasminogen activator are sold in the form of lyophilized preparations that have to be dissolved before use. Since thrombolytic treatment of acute myocardial infarction has to be started as early as possible after onset of the infarction, any time delay caused by such preparation is a problem.

Many efforts have been made to find ways to stabilize the various serine proteases. For trypsin, which degrades itself fairly rapidly, a simple and efficient stabilizing agent is the calcium ion (Sipos T and Merkel J, Biochemistry 9:2766 (1970)). Decreasing the pH to below 4 is also a method that works with some of the enzymes, like trypsin and plasmin, but is not feasible with thrombin, since it is irreversibly inactivated by a pH below 5. Reversible protease inhibitors can be used, but are less popular, since they interfere in a detrimental fashion with the action of the enzyme when they are used by themselves (see below).

For stabilization of tissue plasminogen activator (tPA), addition of the amino acid arginine is conventionally used. The tPA material in clinical use today contains arginine as stabilizer.

Also, a lot of effort has been devoted to find ways to stabilize thrombin solutions. As examples of stabilizing additives, the following proposals may be mentioned: carboxylic acids in high concentrations, EDTA, various amino acids, albumin, polymers such as polyethylene glycol, polyvinyl pyrrolidone and polyvinyl alcohol, glycerol, various inorganic salts, carbohydrates, gelatin, collagen.

Japanese patent application JP2004191367 describes a stabilized thrombin containing test reagent for testing blood coagulation ability. The test reagent contains thrombin and a thrombin inhibitor, and may also comprise one or more thrombin stabilizing compounds selected from calcium ion, an organic acid, a surfactant and a protein.

WO 02/100830, WO 02/22575, WO 00/20394, WO 99/11658, WO 02/37937 and U.S. Pat. No. 5,409,927 all describe different serine protease inhibiting compounds and their use in pharmaceutical compositions for treatment of various disease conditions, such as thrombosis, wherein inhibition of the corresponding serine proteases is indicated.

Nakamura et al. (*J. Chrom. A*, 1009, (2003), 133-139) describe the use of an immobilized protease inhibitor for affinity chromatography of trypsin-like proteases.

Turner et al. (*Biochemistry*, 25, (1986), 4929-4935) describe three p-amidinophenyl esters that irreversibly inhibit human factor IXa.

Tsung Fu Yang et al. (*Biomacromolecules*, 25, (2004), 1926-1932) describe the synthesis of a cationic polymer, N,N-diethylethylenediamin polyurethane, for use in gene delivery.

US patent application 2001/0033837 (corresponding to EP 1 136 084 A1) describes a thrombin preparation containing a non-covalently bound inhibitor as stabilizer. Furthermore, the inhibitor is combined with other stabilizing additives, like sugars or carboxylic acids, which have been previously described in patents or other publications.

JP 2000300250 describes the stabilization of thrombin solutions by addition of polyvinyl alcohol, gelatin or polyvinyl pyrrolidone in different buffer solutions.

In GB 1354761, proteases and amylases are stabilized to various extents by a number of substances, such as aliphatic alcohols, carboxylic acids, heterocyclic compounds containing hydroxyl groups, and aliphatic or alicyclic amines.

Thus, stabilization of a serine protease using inhibitors has been described (for example US 2001/0033837 and JP 2004191367, supra). The problem with this approach is that the inhibitor strongly diminishes the effect of the enzyme, if it is not removed prior to use of the preparation. If a potent inhibitor is used, most of the enzymatic activity is lost. A better approach is to use a reversible inhibitor of intermediate strength. However, even in this case, a considerable part of the initial enzymatic activity will be lost as concentration of the inhibitor is increased in order to get a good stabilization effect.

DISCLOSURE OF THE INVENTION

It is therefore an object of the present invention to accomplish a serine protease composition, which is stable in solution and retains a degree of enzymatic activity which is sufficient for practical use of the composition.

It is another object of the present invention to provide a serine protease composition, which is amenable to direct use without prior steps of preparation from deep frozen or lyophilized material.

It is a further object of the present invention to enable practical use of reversible inhibitors of serine proteases for stabilization purposes, through the provision of an additional stabilizing component.

These, and other objects apparent from the present text, are attained by the different aspects of the present invention as claimed.

Thus, one aspect of the invention provides a stabilized serine protease composition comprising a) a serine protease; b) a reversible inhibitor of said serine protease; and c) a stabilizing agent M having the formula I:

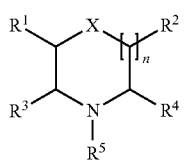

wherein
n is 0, 1 or 2;
X is O, N or $CH_2$;
$R^1$-$R^4$ are the same or different, and selected from H, —$CH_2$—$R^6$, —$CH_2$—O—$R^6$, —$CH_2$—S—$R^6$, —$CH_2$—NH—$R^6$, —CO—O—$R^6$, —CO—NH—$R^6$, —$CH_2$—NH—CO—$R^6$, —$CH_2$—O—CO—$R^6$, —$CH_2$—NH—CO—NH$R^6$, —$CH_2$—NH—CO—O$R^6$, —$CH_2$—NH—CS—NH$R^6$ and —$CH_2$—O—CO—NH$R^6$;
$R^5$ is as $R^1$-$R^4$ or P-Q;
P is selected from —$(CH_2)_m$— and —$(CH_2)_m$—Y—$(CH_2)_m$—, wherein m is 1-6 and Y is O, NH or S;
Q is selected from H, —$SO_3$, —COON, —$NH_2$, —OH and —$CONH_2$;
each $R^6$ individually being selected from H, substituted or non-substituted lower alkyl, substituted or non-substituted cycloalkyl, substituted or non-substituted benzyl, substituted or non-substituted aryl or mono-, bi-, or tricyclic unsubstituted or substituted heteroaromatic ring(s) with one or more heteroatoms and non-aromatic heterocycles, the substituents of the substituted groups being selected from lower alkyl, halogens, substituted or non-substituted aryl, substituted or non-substituted hetero-aromatic compounds, non-aromatic heterocycles, alkyloxy, alkylamino;
or a pharmaceutically acceptable salt thereof.

The present invention derives from initial results from a study on the stability of thrombin, in which it was surprisingly found that the inventive combination of a reversible inhibitor of the enzyme and a stabilizing agent M as defined above had a strong stabilizing effect on the enzyme in solution. Both the thrombin inhibitor and the stabilizing agent M alone had stabilization effects on thrombin, but the combination was several fold better than any of them (see Example 1). Thus, when a low concentration of enzyme inhibitor was combined with morpholine, MOPS or related compounds, a very strong stabilizing effect on the enzyme was obtained. Some tested compositions were stable, as indicated by less than 30% decrease in activity, for more than 2 months at 37° C. This would, according to data in prior publications and confirmed by the present inventors, correspond to 6 months at room temperature or 2.5 years at refrigerator temperature. The results from the initial study were expanded to include experiments on other serine proteases, and in these experiments the surprising stabilizing effect was also observed.

As exemplified below, the composition according to the invention exhibits a substantially improved stability as compared to enzyme compositions without the inventive combination of ingredients b) and c). With the inventive approach, a low concentration of serine protease inhibitor may be used, and a satisfactory degree of stabilization still obtained. For example, the concentration of the inhibitor may be lower than what has been suggested previously, eg in US 2001/0033837. With such a low concentration of inhibitor, much more of the enzymatic activity is retained in the stabilized enzyme solution.

It should be noted that the increase in stabilization due to the combination of the reversible serine protease inhibitor and stabilizing agent M is not regarded as an additional inhibitory effect provided by M. In fact M, as described in Illustrative Example A, may lack any serine protease inhibiting capacity. Without wishing to be bound by theory, the present inventors believe that the surprisingly increased stabilizing effect observed is achieved through a beneficial synergy between reversible serine protease inhibitors and stabilizing agents M of the inventive composition. The present invention provides such a combination of a reversible serine protease inhibitor and stabilizing agent M in a stabilized serine protease composition and use of such a combination for stabilizing a serine protease composition.

In an embodiment of the invention, the serine protease in the composition is selected from the group consisting of trypsin, kallikrein, thrombin, plasmin, urokinase, tissue plasminogen activator, active form of factor IX, active form of factor X and active form of factor XI. In a more specific embodiment, the serine protease is thrombin. In another specific embodiment, the serine protease is plasmin. In yet another specific embodiment, the serine protease is trypsin.

Reversible inhibitors to serine proteases are known to persons of skill in the art, and which one is the optimal to use will vary depending on what specific serine protease is used. In general, it is of importance for the intended effect that the inhibitor is not of great strength. In other words, the inhibitory effect has to be moderate enough that the enzymatic activity remains usefully high. As a guideline, it has been found that inhibitors having a $K_i$ of between 0.01 mM and 2 mM are suitable for use in the composition according to the invention, with from 0.04 mM to 0.5 mM as a preferred range.

In one embodiment, in which the serine protease is thrombin, the reversible inhibitor may be selected from N-(2'-phenoxy)-4-aminopyridin and derivatives thereof, benzamidine, N,N-diethylethylenediamine, aminobenzamidine, amidinopyridin and tert-butylamidin. In another embodiment, in which the serine protease is thrombin, the reversible inhibitor is selected from N-(2'-phenoxy)-4-aminopyridin and derivatives thereof, N,N-diethylethylenediamine, amidinopyridin and tert-butylamidin. In a more specific embodiment, in which the serine protease is thrombin, the reversible inhibitor is N-(2'-phenoxy)-4-aminopyridin or a derivative thereof. In another embodiment, in which the serine protease is plasmin, the reversible inhibitor is selected from N,N-diethylethylenediamine, aminobenzamidine and benzamidine. In another embodiment, in which the serine protease is trypsin, the reversible inhibitor is selected from aminobenzamidine and benzamidine. These combinations of enzymes and inhibitors are illustrative examples, and are not to be interpreted as limiting.

In one embodiment of the invention, the value of n in formula I is 1 or 2. In a more specific embodiment, n in formula I is 1.

The composition according to the invention comprises a stabilizing agent M with the general formula I given above. In embodiments of the invention, stabilizing agent M is a compound of formula II:

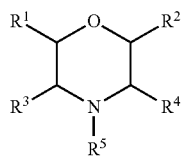

(II)

wherein
$R^1$-$R^4$ are the same or different, and selected from H, —$CH_2$—$R^6$;
$R^5$ is as $R^1$-$R^4$ or P-Q;
P is selected from —$(CH_2)_m$— and —$(CH_2)_m$—Y—$(CH_2)_m$—, wherein m is 1-6 and Y is O, NH or S;
Q is selected from H, —$SO_3$, —COOH, —$NH_2$, —OH and —$CONH_2$;
each $R^6$ individually being selected from H, substituted or non-substituted lower alkyl, substituted or non-substituted cycloalkyl, substituted or non-substituted benzyl, substituted or non-substituted aryl or mono-, bi-, or tricyclic unsubstituted or substituted heteroaromatic ring(s) with one or more heteroatoms and non-aromatic heterocycles, the substituents of the substituted groups being selected from lower alkyl, halogens, substituted or non-substituted aryl, substituted or non-substituted hetero-aromatic compounds, non-aromatic heterocycles, alkyloxy, alkylamino;
or a pharmaceutically acceptable salt thereof.

Accordingly, in some embodiments, stabilizing agent M is a compound of formula III:

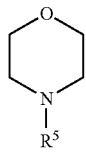

(III)

wherein
$R^5$ is —$CH_2$—$R^6$ or P-Q;
P is selected from —$(CH_2)_m$— or —$(CH_2)_m$—Y—$(CH_2)_m$—, wherein m is 1-6 and Y is O, NH or S;
Q is selected from H, —$SO_3$, —COOH, —$NH_2$, —OH and —$CONH_2$,
each $R^6$ individually being selected from substituted or non-substituted lower alkyl, substituted or non-substituted cycloalkyl, substituted or non-substituted benzyl, substituted or non-substituted aryl, the substituents of the substituted groups being selected from lower alkyl, halogens, substituted or non-substituted aryl, substituted or non-substituted hetero-aromatic compounds, non-aromatic heterocycles, alkyloxy, alkylamino;
or a pharmaceutically acceptable salt thereof.

In some embodiments of the invention, stabilizing agent M is selected from the group consisting of morpholine, 3-(N-morpholino)propanesulfonic acid (MOPS), morpholino butyl sulphonic acid, morpholino propyl carboxylic acid, morpholino ethyl alcohol and morpholino ethyl sulphonic acid. Thus, examples of compounds M for use in the compositions of this aspect of the invention are morpholine and 3-(N-morpholino)propanesulfonic acid (MOPS). In a specific embodiment of the invention, stabilizing agent M is morpholine.

A composition according to the invention which shows the stabilization effect is one in which the serine protease is thrombin, the reversible inhibitor is N-(2'-phenoxy)-4-aminopyridin, and stabilizing agent M is morpholine.

Another composition according to the invention which shows the stabilization effect is one in which the serine protease is thrombin, the reversible inhibitor is N-(2'-phenoxy)-4-aminopyridin, and stabilizing agent M is 3-(N-morpholino)propanesulfonic acid (MOPS).

Another composition according to the invention which shows the stabilization effect is one in which the serine protease is thrombin, the reversible inhibitor is aminobenzamidine, and stabilizing agent M is morpholine.

Another composition according to the invention which shows the stabilization effect is one in which the serine protease is plasmin, the reversible inhibitor is N,N-diethylethylenediamine and stabilizing agent M is morpholine.

Another composition according to the invention which shows the stabilization effect is one in which the serine protease is plasmin, the reversible inhibitor is aminobenzamidine and stabilizing agent M is morpholine.

In serine protease compositions for topical administration, eg to a wound site, it has been a problem that the composition can easily flow or be rinsed from the site where it is applied. In order to solve this problem, it is possible to add to the enzyme composition an adhesive polymer, which then serves the purpose of making the composition more viscous and adherent to skin or wound sites. As an embodiment of the present invention, such an addition of an adhesive polymer to the inventive composition may have an additional unexpected and beneficial effect on its stability. The addition of a polymer then serves the double purpose of increasing the viscosity and adhesiveness of the composition, at the same time as it helps the stabilization of the enzyme even further.

In some embodiments of the invention, the composition further comprises a viscous and adhesive polymer selected from polysaccharides and gelatin. Thus, the polymer may for example be a polysaccharide, such as selected from starch, its derivatives, cellulose, its derivatives, and mixtures thereof. Specific, non-limiting examples of starches useful as additives to the composition according to the invention include corn starch and potato starch and mixtures thereof, whereas non-limiting examples of useful cellulose derivatives are carboxymethyl cellulose and ethyl hydroxyethyl cellulose and mixtures thereof. In a specific embodiment the polysaccharide is carboxymethyl chitosan. In further embodiments of the invention, said polysaccharide is present in a concentration of 0.1-5%. However, it is also envisaged that the polymer is gelatin, such as gelatin from a cold water fish.

In some embodiments of the invention, said gelatin is present in a concentration of 0.5-20%.

In one embodiment of the invention, said serine protease is present in a concentration of 0.001-2 mg/ml. In a more specific embodiment, said serine protease is present in a concentration of 0.01-1 mg/ml.

In one embodiment of the invention, in which the serine protease is thrombin, the concentration of thrombin is between 5-3500 activity units/ml.

In one embodiment of the invention, in which the serine protease is thrombin, the concentration of thrombin is between 200-1000 activity units/ml.

In one embodiment of the invention, in which the serine protease is thrombin, the concentration of thrombin is between 5-20 activity units/ml.

In one embodiment of the invention, said reversible inhibitor of said serine protease is present in a concentration of 0.1-10 mM. In a more specific embodiment, said reversible inhibitor of said serine protease is present in a concentration of 0.5-2 mM.

In one embodiment of the invention, said stabilizing agent M is present in a concentration of 0.02-0.5 M. In a more specific embodiment, said stabilizing agent M is present in a concentration of 0.1-0.3 M.

According to another aspect thereof, the present invention provides use of a composition as described above as a medicament.

Another aspect of the invention concerns use of said composition, in which the serine protease is thrombin, for the preparation of a medicament for establishing haemostasis in a subject suffering from a bleeding. A related aspect of the invention provides a method for establishing haemostasis in a subject suffering from a bleeding, comprising applying a composition according to the invention, in which composition the serine protease is thrombin, to the site of bleeding in an amount sufficient to diminish or stop said bleeding.

In connection with such a use or method employing a thrombin composition according to the invention as a medicament, the stability of the inventive composition offers benefits in the circumstances in which it is used. Often, thrombin compositions are used in the context of emergency situations, wherein it is crucial to stop subjects from bleeding. In these same situations, the use of conventional, haemostatic thrombin preparations is difficult, since they often require cumbersome and time-consuming steps of thawing (if frozen) and/or dissolution (if lyophilized). The present invention enables the production of eg such haemostatic agents in the form of solutions, whose stability is such that they can readily be stored during extended periods of time, for example in an ambulance or an emergency helicopter, until needed at the site of an accident or the like. At this time, they may be used as is, without any delay due to preparation.

The conventional preparations used to stop bleeding contain fairly high concentrations of thrombin, between 200-1000 activity units/ml. In connection with plastic surgery applications, this is seen as a risk for increased scar formation. Low thrombin concentration solutions are presently prepared in the clinic by dilution of concentrated thrombin solutions. No ready to use preparation is available. Therefore, in a further aspect thereof, the present invention provides a stabilized thrombin composition with a considerably lower concentration of thrombin, between 5-20 activity units/ml, and use thereof in plastic surgery.

Another aspect of the invention exploits the known properties of plasmin, urokinase or tPA as thrombolytic agents. Thus, the invention provides use of a composition as described above, in which the serine protease is selected from plasmin, urokinase and tissue plasminogen activator, for the preparation of a medicament for thrombolytic treatment. A related aspect provides a method for thrombolytic treatment in a subject in need thereof, comprising administering a composition as described above, in which composition the serine protease is selected from plasmin, urokinase and tissue plasminogen activator, to the subject in an amount sufficient for said treatment. In these two related aspects, the thrombolytic treatment in question may, as non-limiting examples, be performed in order to treat myocardial infarction or in order to treat stroke.

As mentioned in the context of the composition aspect of the invention, the increase in stabilization due to the combination of the reversible serine protease inhibitor and stabilizing agent M is not regarded as an additional inhibitory effect provided by M. In fact M, as described in Illustrative Example A, may lack any serine protease inhibiting capacity. Without wishing to be bound by theory, the present inventors believe that the surprisingly increased stabilizing effect observed is achieved through a beneficial synergy between reversible serine protease inhibitors and stabilizing agents M of the inventive composition.

Therefore, in another aspect thereof, the invention provides the use of a combination of
  a) a reversible serine protease inhibitor and
  b) a stabilizing agent M of formula I:

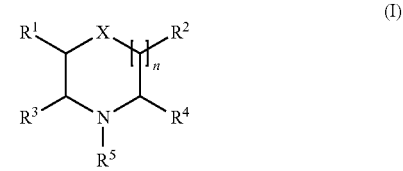

wherein
  n is 0, 1 or 2;
  X is O, N or $CH_2$;
  $R^1$-$R^4$ are the same or different, and selected from H, —$CH_2$—$R^6$, —$CH_2$—O—$R^6$, —$CH_2$—S—$R^6$, —$CH_2$—NH—$R^6$, —CO—O—$R^6$, —CO—NH—$R^6$, —$CH_2$—NH—CO—$R^6$, —$CH_2$—O—CO—$R^6$, —$CH_2$—NH—CO—NHR$^6$, —$CH_2$—NH—CO—OR$^6$, —$CH_2$—NH—CS—NHR$^6$ and —$CH_2$—O—CO—NHR$^6$;
  $R^5$ is as $R^1$-$R^4$ or P-Q;
  P is selected from —$(CH_2)_m$— and —$(CH_2)_m$—Y—$(CH_2)_m$—, wherein m is 1-6 and Y is O, NH or S;
  Q is selected from H, —$SO_3$, —COON, —$NH_2$, —OH and —$CONH_2$;
  each $R^6$ individually being selected from H, substituted or non-substituted lower alkyl, substituted or non-substituted cycloalkyl, substituted or non-substituted benzyl, substituted or non-substituted aryl or mono-, bi-, or tricyclic unsubstituted or substituted heteroaromatic ring(s) with one or more heteroatoms and non-aromatic heterocycles, the substituents of the substituted groups being selected from lower alkyl, halogens, substituted or non-substituted aryl, substituted or non-substituted hetero-aromatic compounds, non-aromatic heterocycles, alkyloxy, alkylamino; or a pharmaceutically acceptable salt thereof;
  for stabilizing a serine protease composition, wherein the reversible serine protease inhibitor and the stabilizing agent M act in synergy to provide a serine protease stabilizing effect.

In this inventive use of a combination of a reversible serine protease inhibitor and a stabilizing agent for stabilization of a serine protease composition, the choices of particular components that may be used and substituents for compounds M are as discussed above in relation to the composition aspect of the invention.

In yet another aspect, the invention provides a method for the stabilization of a serine protease, which comprises admixing the serine protease with a) a reversible inhibitor of said serine protease; and b) a stabilizing agent M of formula I:

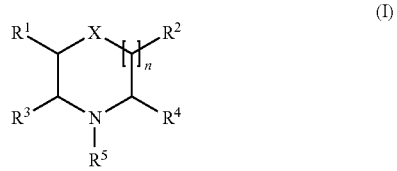

wherein
n is 0, 1 or 2;
X is O, N or $CH_2$;
$R^1$-$R^4$ are the same or different, and selected from H, —$CH_2$—$R^6$, —$CH_2$—O—$R^6$, —$CH_2$—S—$R^6$, —$CH_2$—NH—$R^6$, —CO—O—$R^6$, —CO—NH—$R^6$, —$CH_2$—NH—CO—$R^6$, —$CH_2$—O—CO—$R^6$, —$CH_2$—NH—CO—NH$R^6$, —$CH_2$—NH—CO—O$R^6$, —$CH_2$—NH—CS—NH$R^6$ and —$CH_2$—O—CO—NH$R^6$;
$R^5$ is as $R^1$-$R^4$ or P-Q;
P is selected from —$(CH_2)_m$— and —$(CH_2)_m$—Y—$(CH_2)_m$—, wherein m is 1-6 and Y is O, NH or S;
Q is selected from H, —$SO_3$, —COON, —$NH_2$, —OH and —$CONH_2$;
each $R^6$ individually being selected from H, substituted or non-substituted lower alkyl, substituted or non-substituted cycloalkyl, substituted or non-substituted benzyl, substituted or non-substituted aryl or mono-, bi-, or tricyclic unsubstituted or substituted heteroaromatic ring(s) with one or more heteroatoms and non-aromatic heterocycles, the substituents of the substituted groups being selected from lower alkyl, halogens, substituted or non-substituted aryl, substituted or non-substituted hetero-aromatic compounds, non-aromatic heterocycles, alkyloxy, alkylamino; or a pharmaceutically acceptable salt thereof.

In this inventive method for stabilization of a serine protease composition, the choices of particular components that may be used and substituents for compounds M are as discussed above in relation to the composition aspect of the invention.

A further aspect of the invention concerns the use of the composition as described above for adsorption onto a solid object, in order that this solid object may provide the enzymatic activity in question. In particular, it is of interest in many surgical applications to enter and, in particular, exit arteries while inflicting as little damage from bleeding as possible. In order to stop bleeding from an artery, it has previously been suggested to use a form of "arterial plug" (such objects are also known as vascular sealing devices, femoral access closure devices (when the femoral artery is used for entry, eg in angiography), vascular hemostasis devices and puncture closure devices), for example made from collagen or another biodegradable material. According to the present aspect of the invention, such a plug may advantageously be coated with a composition according to the invention, in which the serine protease is thrombin. Such a plug achieves faster sealing of the opening of the artery, in that the thrombin of the composition aids in blood clotting around the plug. Thus, the invention provides, in this aspect, a vascular haemostasis device having an amount of the composition according to the invention, in which the serine protease is thrombin, adsorbed on it. The vascular haemostasis device is preferably made from a biodegradable solid or semi-solid material, such as collagen, chitosan or other biological polymer.

Another aspect of the invention concerns the novel identification of N,N-diethylethylenediamine as a serine protease inhibitor. Thus, in this aspect, the invention provides use of N,N-diethylethylenediamine as an inhibitor of a serine protease, as well as a method of inhibiting a serine protease, comprising admixing therewith an inhibitory amount of N,N-diethyl-ethylenediamine. In some embodiments of this aspect of the invention, the serine protease is plasmin. In other embodiments of this aspect of the invention, the serine protease is thrombin.

It is generally preferred, for the realization of all the advantages of the invention's different aspects, that the composition according to the invention is in a form selected from a solution and a gel. In this regard, aqueous solutions and aqueous gels are more preferred.

DEFINITIONS

As used herein, the term "lower alkyl" means an unbranched or branched, cyclic, saturated or unsaturated (alkenyl or alkynyl)hydrocarbyl radical which may be substituted or unsubstituted. Where cyclic, the alkyl group is preferably C3-C12, more preferably C5-C10, most preferably C5-C7. Where acyclic, the alkyl group is preferably C1-C10, more preferably C1-C6, more preferably methyl, ethyl, propyl (n-propyl, isopropyl), butyl (branched or unbranched) or pentyl, most preferably methyl.

As used herein, the term "aryl" means an aromatic group, such as phenyl or naphthyl, or a mono-, bi-, or tricyclic heteroaromatic group containing one or more heteroatom(s) preferably selected from N, O and S, such as pyridyl, pyrrolyl, quinolinyl, furanyl, thienyl, oxadiazolyl, thiadiazolyl, thiazolyl, oxazolyl, pyrazolyl, triazolyl, tetrazolyl, isoxazolyl, isothiazolyl, imidazolyl, pyrimidinyl, indolyl, pyrazinyl, indazolyl, pyrimidinyl, thiophenetyl, pyranyl, carbazolyl, acridinyl, quinolinyl, benzoimidazolyl, benzthiazolyl, purinyl, cinnolinyl, pterdinyl.

As used herein, the term "functional group" means, in the case of unprotected: hydroxy-, thiolo-, aminofunction, carboxylic acid, and in the case of protected: lower alkoxy, N—, O—, S— acetyl, carboxylic acid ester.

As used herein, the term "heteroaryl" means an aromatic group containing one or more heteroatom(s) preferably selected from N, O and S, such as pyridyl, pyrrolyl, quinolinyl, furanyl, thienyl, oxadiazolyl, thiadiazolyl, thiazolyl, oxazolyl, pyrazolyl, triazolyl, imidazolyl, pyrimidinyl, indolyl, pyrazinyl or indazolyl.

As used herein, the term "non-aromatic heterocycle" means a non-aromatic cyclic group containing one or more heteroatom(s) preferably selected from N, O and S, such as a cyclic amino group such as pyrrolidinyl, piperidyl, piperazinyl, morpholinyl or a cyclic ether such as tetrahydrofuranyl, monosaccharide.

As used herein, the term "halogen" means fluorine, chlorine, bromine or iodine.

As used herein, the term "substituted" means that the groups concerned are substituted with a functional group such as hydroxyl, amine, sulfide, silyl, carboxylic acid, halogen, aryl, etc.

Examples of pharmaceutically acceptable addition salts for use in the compositions of the present invention include those derived from mineral acids, such as hydrochlorid, hydrobromic, phosphoric, metaphosphoric, nitric and sulphuric acids, and organic acids, such as tartaric, acetic, citric, malic, lactic, fumaric, benzoic, glycolic, gluconic, succinic, and arylsulphonic acids. Pharmaceutically acceptable excipients described herein, for example, vehicles, adjuvants, carriers or diluents, are well known to those who are skilled in the art and are readily available to the public. A pharmaceutically acceptable carrier may be one which is chemically inert to the active compounds and which have no detrimental side effects or toxicity under the conditions of use. Pharmaceutical formulations may be found eg in Remington: The Science and Practice of Pharmacy, 19$^{th}$ edition, Mack Printing Company, Easton, Pa. (1995).

As detailed in the description of the invention, a possible choice of inhibitor for use in the composition and methods according to the invention is "N-(2'-phenoxy)-4-aminopyridin and derivatives thereof". By this is meant a compound having the formula IV:

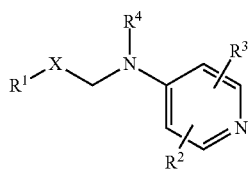

wherein
  $R^1$ is selected from H, C1-C6-alkyl, C3-C7-cyclo alkyl, phenyl, benzyl acetyl and benzoyl;
  X is selected from oxygen, nitrogen and sulfur;
  $R^2$ and $R^3$ is each individually selected from H, halogen, hydroxyl, C1-C6-alkyl, C3-C7-cyclo alkyl, C1-C6-alkyloxy; and
  $R^4$ is selected from H, C1-C6-alkyl, arylalkyl and acyl.

Preferred such inhibitors have the formula V:

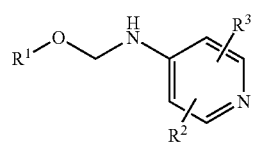

wherein
  $R^1$ is selected from C1-C6-alkyl, C3-C7-cyclo alkyl, phenyl and benzyl;
  $R^2$ and $R^3$ is each individually selected from H, halogen, hydroxyl, C1-C6-alkyl, C3-C7-cyclo alkyl and C1-C6-alkyloxy.

EXAMPLES

The following examples illustrate the invention, and are not to be interpreted as limiting.

In the following description of experiments conducted in accordance with the present invention, the time it takes to reach 70% of the initial activity is used as a numerical value for the stability of an enzyme solution. This value, denoted "T 70%", is chosen since it corresponds to what could be accepted as a maximum permitted loss in activity during a life span of a commercial product.

In the experimental studies, a high temperature (37° C.) has been used, as well as a high concentration of enzyme. This has been made in order to obtain stability data in reasonably short times, and not have to wait for months or years. The stability's dependency on temperature has been studied, and the results given in Example 1. This study showed that the inactivation process is about 3 times slower at room temperature, and around 20 times slower at refrigerator temperature, than the process actually measured (at 37° C.).

Furthermore, the inactivation process is concentration dependent, and is more rapid at higher concentrations of the enzyme. The concentration of thrombin used in Example 1 was 1 mg/ml (or 3300 units/ml), ie higher than the 0.1-0.3 mg/ml used in present commercially available preparations and/or devices. Studies of the concentration dependency has shown that the inactivation process is 3-4 times slower at those concentrations as compared to the concentration used in Example 1.

Taking this together would give a factor of between 10-12, with which to multiply the T 70% value in order to arrive at what corresponds to room temperature storage conditions for a commercial product containing a serine protease, such as a haemostatic preparation containing thrombin. In Table 1, the composition with N-(2'-phenoxy)-4-aminopyridine and MOPS has a T 70% of 120 days. That would correspond to a value, for a 0.1-0.3 mg/ml product, of more than 1200 days in room temperature conditions, ie more than three years. This clearly exceeds anything previously accomplished, regarding the stabilization of thrombin in solution.

Example 1

Stabilization of Human Thrombin

To determine the coagulant activity of thrombin solutions, the time to clotting of a fibrinogen solution (1.3 mg/ml) after additions of various dilutions of a solution of a particular human thrombin (derived from plasma, 3300 units/mg, Biovitrum AB, Sweden) was measured. The clotting times were measured using an Amelungen Kc 1 coagulometer (Amelungen, Germany). To study the stabilities of thrombin solutions with different additives, the samples were incubated in a thermostat chamber kept at 37° C. Aliquots were taken out at various time intervals, and the remaining thrombin activity in these aliquots was measured. From the values obtained, activity decay curves could be constructed.

Activity decay curves of 1 mg/ml thrombin solutions in 10 mM HEPES, 0.13 M NaCl buffer, pH 7.4, showed T 70% values around 1.6 days at 37° C. Corresponding experiments at room temperature (around 21° C.) showed a T 70% value of 5.4 days, whereas after refrigerator storage (around 5° C.), the T 70% value was 36 days. Thus, as expected, there is a strong temperature dependency.

Solutions containing 1 mg/ml of thrombin in 10 mM HEPES and 0.13 M NaCl at pH 7.4 with the indicated stabilizing additive(s) were put in the thermostat chamber, and their activity decay curves were determined. The results obtained are shown in Table 1. Data on the corresponding 1 mg/ml thrombin solution without additives is included for comparison.

TABLE 1

Stabilization of thrombin

| Stabilizing additive(s) | T 70% (days) |
|---|---|
| None | 1.6 |
| 0.20M MOPS | 7.5 |
| 0.20M morpholine | 8.5 |
| 0.20M morpholino butyl sulphonic acid | 4.0 |
| 0.20M morpholino propyl carboxylic acid | 4.1 |
| 0.20M morpholino ethyl alcohol | 3.8 |
| 0.20M morpholino ethyl sulphonic acid | 3.2 |
| 0.5 mM aminobenzamidine | 20 |
| 0.20M MOPS + 0.5 mM aminobenzamidine | 68 |
| 3.1 mM N-(2'-phenoxy)-4-aminopyridin | 74 |
| 1.9 mM N-(2'-phenoxy)-4-aminopyridin | 35 |
| 1.9 mM N-(2'-phenoxy)-4-aminopyridin + 0.5 mM aminobenzamidine | 68 |
| 0.20M MOPS + 1.9 mM N-(2'-phenoxy)-4-aminopyridin | 120 |
| 0.20M N,N-diethylethylenediamine | 10 |
| 0.20M MOPS + 0.20M N,N-diethylethylenediamine | 22 |

It is evident that the tested compounds all have a stabilizing effect. However, there is a synergistic effect of combinations of inhibitor and morpholine-containing compound in accordance with the invention, as evidenced by the superior results obtained with such combinations. As the table above illustrates, the addition of 0.20 M MOPS alone gives an increase in stabilization by a factor of 4.7, and the addition of 0.5 mM of the reversible thrombin inhibitor aminobenzamidine gives a stabilization increase by a factor of 12.5. The inventive combination, however, stabilizes the thrombin composition much better, by a factor of 42.5. The inventive combination of MOPS and N,N-diethylethylenediamine is also better at stabilizing the enzyme than the individual components. Likewise, the combination of 0.20 M MOPS and 1.9 mM N-(2'-phenoxy)-4-aminopyridin is seen to confer a very high stabilization increase, a factor of 75, whereas the individual components increase stability by a factor of 4.7 and 22, respectively.

The thrombin used in the study is human thrombin derived from plasma. Recombinant human thrombin has also been studied and has essentially shown the same behavior.

Example 2

Stabilization of Bovine Thrombin

Stabilization of bovine thrombin was studied. The experimental setup was the same as in Example 1, but the concentration of bovine thrombin (Baxter) used was 0.4 mg/ml. Upon storage at 37° C., the thrombin solution in HEPES buffer showed a T 70% value of 1.3 days. The thrombin solution in HEPES buffer plus 3.0 mM N-(2'-phenoxy)-4-aminopyridin and 0.20 M MOPS showed a T 70% value of 54 days.

The results obtained show that bovine thrombin is somewhat more labile than the preparations of human thrombin studied, but that a very good stabilizing effect is nevertheless obtained by the compositions of the invention.

Example 3

Low Concentrations of Thrombin

Stabilization of thrombin in compositions containing low concentrations of thrombin was studied. The stabilizing effect of the compositions according to the invention was demonstrated to work also for comparatively low concentrations of thrombin.

A 15.0 activity units/ml solution of human thrombin (derived from plasma, 3300 units/mg, Biovitrum AB, Sweden) in HEPES buffer, pH 7.4, showed a T 70% value of 23 days. The corresponding solution in HEPES buffer, pH 7.4, plus 2.0 mM N-(2'-phenoxy)-4-aminopyridin and 0.20 M MOPS exhibited a T 70% value of 92 days.

Example 4

Stabilization of Plasmin

The stabilization of solutions of plasmin in accordance with the invention was tested. The activity of plasmin was determined using chromogenic peptide substrate Chromozym TH (Pentapharm, Switzerland) and measurement of absorbance change at 405 nm in a spectrophotometer. Solutions containing 100 µg/ml of plasmin (specific activity 3.2 units/mg, Sigma-Aldrich) in 10 mM HEPES and 0.13 M NaCl, pH 7.4, as well as stabilizers as indicated in Table 2 below were incubated at 37° C., and samples were taken out at various time intervals for activity determination. The results obtained are shown in Table 2.

TABLE 2

Stabilization of plasmin

| Stabilizing additive(s) | T 70% (hours) |
|---|---|
| None | 3 |
| 0.20M morpholine | 12 |
| 0.13M N,N-diethylethylenediamine | 8 |
| 1 mM benzamidine | 16 |
| 1.3 mM aminobenzamidine | 52 |
| 0.20M morpholine + 0.13M N,N-diethylethylenediamine | 22 |
| 0.20M morpholine + 1.3 mM aminobenzamidine | 216 |

From these results, it is evident that a very strong stabilization is obtained using the combination in accordance with the invention. 0.20 M morpholine increases the stability of the plasmin composition by a factor of 4, 0.13 M N,N-diethylethylenediamine by a factor of 2.7 and 1.3 mM aminobenzamidine by a factor of 17. However, the combination of morpholine and N,N-diethylethylenediamine increases the stability of the plasmin composition by a factor of 7.3, and the combination of morpholine and aminobenzamidine increases the stability by a factor of 72.

Example 5

Stabilization of Trypsin

The stabilization of solutions of trypsin in accordance with the invention was tested. The activity of trypsin was determined using tosyl arginine methyl ester (TAME) as substrate and measuring the absorbance change at 247 nm in a spectrophotometer. Solutions containing 100 µg/ml of trypsin (TPCK-treated, Sigma-Aldrich) in 10 mM HEPES and 0.13 M NaCl, pH 7.4, as well as stabilizers as indicated in Table 3 below were incubated at 37° C., and samples were taken out at various time intervals for activity determination. The results obtained are shown in Table 3.

TABLE 3

Stabilization of trypsin

| Stabilizing additive(s) | T 70% (hours) |
|---|---|
| None | 0.6 |
| 0.5M morpholine | 8 |
| 1 mM benzamidine | 43 |
| 0.5M morpholine + 1 mM benzamidine | 88 |

Again, the stabilizing effect is the greatest in the composition according to the invention. Thus, 0.5 M morpholine alone gives an increase in stabilization by a factor of 13, and 1 mM benzamidine alone gives an increase in stabilization by a factor of 72. The inventive combination, on the other hand, gives an increase in stabilization by a factor of 147.

Example 6

Stabilization of Thrombin with CMC

Tests of thrombin solutions containing between 1.0 and 2.0% carboxymethyl cellulose (CMC) for their adhesiveness to human skin showed that the addition of CMC increased both viscosity and adhesiveness strongly. Surprisingly, however, it was also found that the stability of these thrombin solutions was further increased. A 1 mg/ml human thrombin (derived from plasma, 3300 units/mg, Biovitrum AB, Sweden) solution in 0.5 mM aminobenzamidine, 0.20 M MOPS, 10 mM HEPES, 0.13 M NaCl being 2.0% with respect to CMC was incubated at 37° C., and the activity decay curve was determined. The T 70% value obtained was 175 days.

Example 7

Stabilization with Other Adhesive Polymers

Four other polymers were also studied: ethyl hydroxyethyl cellulose (EHEC), potato starch, corn starch and cold water fish gelatin. All four of these polymers increased the adhesiveness and viscosity of thrombin solutions. The compatibility and stability of thrombin solutions with the polymers were further studied by incubation at 37° C. of 1 mg/ml human thrombin (derived from plasma, 3300 units/mg, Biovitrum AB, Sweden) solutions in 0.20 M MOPS, 0.5 mM aminobenzamidine, 10 mM HEPES, 0.13 M NaCl, pH 7.4, containing the various polymers. The concentrations of the polymers used were: EHEC, 0.6%; the two different starches, 4.0%; and gelatin, 12.8%. EHEC was fully compatible with thrombin, and the same T 70% value, i.e. around 65 days, was obtained as with the corresponding solution without EHEC. The starch containing solutions had T 70% values of 22 and 26 days. The stability of thrombin was very good in gelatin with a T 70% value of more than 90 days, which demonstrates additional stabilizing effect of cold water fish gelatin.

Example 8

Bleeding Experiments

The ability of inventive compositions to stop bleeding was tested in a series of experiments on rabbits. The model chosen was incisions in the liver which is a frequently used model. The abdomen of the rabbit was opened and the liver exposed. Standardized cuts of 3 mm length were made in the liver surface and an 0.10 ml amount of test solution was applied to the wound using a syringe. The time to haemostasis was measured. 10-12 experiments were performed with each solution. An average value of bleeding time was calculated after removal of the highest and the lowest value in each series of experiments. For comparison, the commonly used haemostatic agent Tisseel (Baxter), a fibrin glue, was also included in the study. Tisseel was used essentially according to the manufacturer's recommendations. 0.2 ml of solution was applied to each wound using a double syringe with a mixing chamber. The results obtained are given in Table 4 below.

TABLE 4

Bleeding experiments

| Composition | Average bleeding time (s) |
|---|---|
| 10 mM HEPES, 0.13M NaCl, pH 7.4 | 106 |
| 10 mM HEPES, 0.13M NaCl, pH 7.4 + 1.5% CMC | 65 |
| 10 mM HEPES, 0.13M NaCl, pH 7.4 + 1.5% CMC + 0.20M MOPS + 1000 units/ml thrombin | 31 |
| 10 mM HEPES, 0.13M NaCl, pH 7.4 + 2 mM aminobenzamidine + 0.20M MOPS + 1000 units/ml thrombin | 26 |
| Tisseel (Baxter) 0.2 ml solution | 31 |

As is evident from these results, the thrombin solution stabilized according to the invention is the most effective in quickly establishing haemostasis in a bleeding subject, comparable to or better than a commonly used agent.

Example 9

Compatibility with Porous Materials

A solution containing 0.4 mg/ml human thrombin (derived from plasma, 3300 units/mg, Biovitrum AB, Sweden) in 10 mM HEPES, 0.14 M NaCl, 0.5 mM aminobenzamidine, 0.20 M MOPS of pH 7.4 was adsorbed into a piece of polyurethane plaster (marketed as Ligasone by Hartmann Scandicare AB, Anderstorp, Sweden). An amount of solution sufficient to saturate the polyurethane piece was used. The piece was transferred to a tube, which was then closed to prevent evaporation. The tube was kept at 37° C., and samples of solution were taken out at intervals by a slight pressure on the polyurethane piece. The activity decay curve showed a T 70% value of 74 days, corresponding to a stability increase by a factor of 46.

Example 10

Adsorption of Enzyme onto a Solid Phase

Adsorption of thrombin in stabilizing solutions to surfaces was tested. Solid flakes of chitosan (at least 85% deacetylated, Sigma-Aldrich), around 3×3 mm, were incubated for 10 minutes in solutions of 400 units/ml human thrombin (derived from plasma, 3300 units/mg, Biovitrum AB, Sweden) in 10 mM HEPES, 0.13 M NaCl, pH 7.4. The solutions had the following additions: 1) none, 2) 0.10 M morpholine, 2 mM N-(2'-phenoxy)-4-aminopyridine, 3) 0.10 M morpholine, 2 mM N-(2'-phenoxy)-4-aminopyridine, 0.5% carboxymethyl cellulose. The flakes were then taken up and dried on filter paper. To get a measure of thrombin clotting activity, a flake was put in a test tube and 0.4 ml of 1.3 mg/ml fibrinogen solution was added. To improve clot detection, the tube also contained a small steel ball. The clotting times obtained initially on flakes from the various incubation mixtures varied between 1 to 4 minutes. After incubation in Eppendorf tubes at 37° C. for 7 days, the clotting times for flakes incubated in solution 1) were strongly prolonged. The values were between 24 and 27 minutes. In contrast, the clotting times for flakes incubated in solutions 2) and 3) were in the range of from 1 to 2.5 minutes, ie the same as the starting values. Evidently, a strong stabilization of thrombin activity is obtained by using solutions 2) and 3). To test the in vivo haemostatic activity chitosan flakes incubated in solution 3) were applied to wounds in rabbit liver according to the animal model described in Example 8. The average time to haemostasis was 27 seconds (based on six experiments).

Illustrative Example A

Morpholine is not a Thrombin Inhibitor

The possibility that morpholine is an inhibitor of thrombin was evaluated. The fibrinogen clotting activity of thrombin is usually measured by clotting tests, wherein the time to coagulation of a fibrinogen solution is detected by mechanical or optical devices. The clotting tests in this experimental setup were performed in 0.01 M HEPES, 0.13 M NaCl buffer of pH 7.4, which is according to standard procedure (EU Pharmacopeia). A human thrombin (derived from plasma, 3300 units/mg, Biovitrum AB, Sweden) solution containing 89 units/ml was used and dilutions of 1/5, 1/10 and 1/16 were tested. Solutions of various concentrations of morpholine were prepared in the HEPES buffer by adding a concentrated morpholine solution adjusted to pH 7.4. When morpholine is dissolved in water, the pH goes up to 9-10, so HCl was added to get a pH of 7.4. That also increased the ionic strength of the solution. Table I shows the results obtained. Observed clotting times were converted to concentrations of thrombin using a standard curve.

TABLE 5

Inhibitory effect of morpholine

| Morpholine concentration (M) | NaCl added (M) | Apparent thrombin concentration (U/ml) | Apparent inhibition (%) |
|---|---|---|---|
| 0 | 0 | 89 | 0 |
| 0.05 | 0 | 87 | 4 |
| 0.10 | 0 | 71 | 20 |
| 0.15 | 0 | 49 | 45 |
| 0.20 | 0 | 51 | 43 |
| 0 | 0.05 | 74 | 17 |
| 0 | 0.10 | 53 | 40 |
| 0 | 0.15 | 58 | 34 |
| 0 | 0.20 | 55 | 37 |

As evident from these results, there was a prolongation of clotting times with increasing concentration of morpholine up to a certain level. However, the same thing was observed when the ionic strength was increased with NaCl, and a similar profile was exhibited. Thus, the prolongation effect was, in all likelihood, caused by the increase in ionic strength. Further, it is known that an increase of ionic strength from 0.15 M to 0.22 M causes a change in the polymerization of fibrin (B. Blomback, Thrombosis Research, vol. 83, (1996), p. 1-75, especially p. 18). This actually corresponds to the range studied in this experimental series, in which the initial concentration of NaCl was 0.13 M and then increased to 0.18 M and onwards up to 0.33 M. This also corresponds to the plateau level observed. In conclusion, morpholine itself is not an inhibitor of thrombin.

The invention claimed is:

1. A stabilized serine protease composition comprising an aqueous solution of
    a) thrombin;
    b) a reversible inhibitor of thrombin which exhibits a $K_i$ value of between 0.01 and 2 mM; and
    c) a stabilizing agent M, wherein M is 3-(N-morpholino) propane sulfonic acid and M is present in a concentration in the range of 0.1-0.3 M.

2. The composition according to claim 1, in which said thrombin is human thrombin.

3. The composition according to claim 1, which further comprises a viscous and adhesive polysaccharide.

4. The composition according to claim 3, in which the polysaccharide is selected from starch, its derivatives, cellulose, its derivatives, and mixtures thereof.

5. The composition according to claim 4, in which the polysaccharide is selected from carboxymethyl cellulose, ethyl hydroxyethyl cellulose and mixtures thereof.

6. The composition according to claim 3, in which the polysaccharide is carboxymethyl chitosan.

7. The composition according to claim 3, in which said polysaccharide is present in a concentration of 0.1-5%.

8. A composition according to claim 7, in which said polysaccharide is present in a concentration of 1.0-2.0%.

9. The composition according to claim 1, in which thrombin is present in a concentration of 0.001-2 mg/ml.

10. The composition according to claim 1, in which the concentration of thrombin is 5-3500 activity units/ml.

11. The composition according to claim 10, in which the concentration of thrombin is 200-1000 activity units/ml.

12. The composition according to claim 10, in which the concentration of thrombin is 5-20 activity units/ml.

13. The composition according to claim 1, in which said reversible inhibitor of thrombin is present in a concentration of 0.1-10 mM.

14. The composition according to claim 1, in which the reversible inhibitor exhibits a $K_i$ value between 0.04 mM and 0.5 mM.

15. The composition according to claim 1, in which the reversible inhibitor is selected from benzamidine, N,N-diethylethylenediamine, aminobenzamidine, amidinopyridin, tert-butylamidin, and a compound having the formula IV:

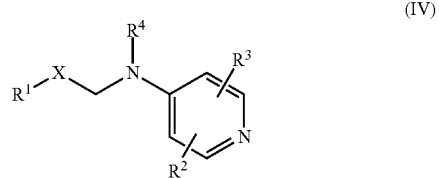

(IV)

wherein
$R^1$ is selected from H, $C_1$-$C_6$-alkyl, $C_3$-$C_7$-cyclo alkyl, phenyl, benzyl acetyl and benzoyl;
X is selected from oxygen, nitrogen and sulfur;
$R^2$ and $R^3$ is each individually selected from H, halogen, hydroxyl, $C_1$-$C_6$-alkyl, $C_3$-$C_7$-cyclo alkyl, $C_1$-$C_6$-alkyloxy; and
$R^4$ is selected from H, $C_1$-$C_6$-alkyl, arylalkyl and acyl.

16. The composition according to claim 15, in which the reversible inhibitor is selected from N,N-diethylethylenediamine, amidinopyridin, tert-butylamidin, and a compound having the formula IV:

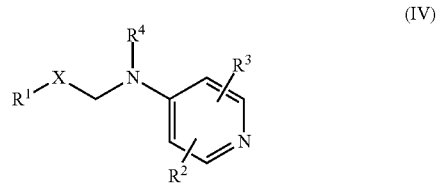

(IV)

wherein
$R^1$ is selected from H, $C_{1-6}$-alkyl, $C_3$-$C_7$-cyclo alkyl, phenyl, benzyl acetyl and benzoyl;

X is selected from oxygen, nitrogen and sulfur;

$R^2$ and $R^3$ is each individually selected from H, halogen, hydroxyl, $C_1$-$C_6$-alkyl, $C_3$-$C_7$-cyclo alkyl, $C_1$-$C_6$-alkyloxy; and $R^4$ is selected from H, $C_{1-6}$-alkyl, arylalkyl and acyl.

17. The composition according to claim 15, in which the reversible inhibitor is a compound having the formula IV:

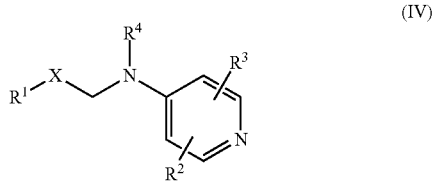

(IV)

wherein $R^1$ is selected from H, $C_{1-6}$-alkyl, $C_3$-$C_7$-cyclo alkyl, phenyl, benzyl acetyl and benzoyl;

X is selected from oxygen, nitrogen and sulfur;

$R^2$ and $R^3$ is each individually selected from H, halogen, hydroxyl, $C_1$-$C_6$-alkyl, $C_3$-$C_7$-cyclo alkyl, $C_1$-$C_6$-alkyloxy; and $R^4$ is selected from H, $C_{1-6}$-alkyl, arylalkyl and acyl.

18. A stabilized serine protease composition comprising an aqueous solution of
   a) thrombin, wherein said thrombin is present in a concentration of 0.001-2 mg/ml;
   b) a reversible inhibitor of thrombin, wherein said reversible inhibitor of thrombin is present in a concentration of 0.1-10 mM; and
   c) a stabilizing agent M, wherein M is 3-(N-morpholino) propanesulfonic acid and M is present in a concentration in the range of 0.1-0.3 M.

* * * * *